(12) United States Patent
Ingalls et al.

(10) Patent No.: US 9,962,522 B2
(45) Date of Patent: May 8, 2018

(54) BRAID PLATING METHOD FOR TORSIONAL STIFFNESS

(71) Applicant: General Metals Corporation, Anoka, MN (US)

(72) Inventors: Craig Ingalls, Burnsville, MN (US); Dennis Gavranovich, Golden Valley, MN (US)

(73) Assignee: Professional Plating, Inc., Anoka, MN (US)

(*) Notice: Subject to any disclaimer, the term of this patent is extended or adjusted under 35 U.S.C. 154(b) by 327 days.

(21) Appl. No.: 14/926,585

(22) Filed: Oct. 29, 2015

(65) Prior Publication Data

US 2016/0121077 A1 May 5, 2016

Related U.S. Application Data

(60) Provisional application No. 62/072,352, filed on Oct. 29, 2014.

(51) Int. Cl.
*A61M 25/00* (2006.01)
*B23P 15/00* (2006.01)
*A61M 25/09* (2006.01)

(52) U.S. Cl.
CPC ...... *A61M 25/005* (2013.01); *A61M 25/0012* (2013.01); *B23P 15/00* (2013.01); *A61M 25/0045* (2013.01); *A61M 2025/09091* (2013.01); *A61M 2025/09133* (2013.01); *A61M 2025/09191* (2013.01); *Y10T 29/49865* (2015.01); *Y10T 29/49982* (2015.01)

(58) Field of Classification Search
CPC ............ A61M 25/005; A61M 25/0045; A61M 25/0012; A61M 2025/09133; A61M 2025/09091; A61M 2025/09191; Y10T 29/49982; Y10T 29/49865; B23P 15/00
See application file for complete search history.

(56) References Cited

U.S. PATENT DOCUMENTS

| | | | |
|---|---|---|---|
| 3,148,072 A | 9/1964 | West et al. | |
| 3,338,726 A | 8/1967 | Berzins | |
| 3,719,508 A | 3/1973 | Gulla et al. | |
| 3,745,039 A | 7/1973 | Feldstein | |
| 3,754,939 A | 8/1973 | Perlstein et al. | |
| 3,915,717 A | 10/1975 | Feldstein et al. | |
| 4,152,164 A | 5/1979 | Gulla et al. | |
| 4,665,604 A * | 5/1987 | Dubowik .......... | A61M 25/0012 138/125 |
| 5,755,704 A * | 5/1998 | Lunn ................. | A61M 25/0012 600/585 |
| 5,897,567 A | 4/1999 | Resseman et al. | |

(Continued)

*Primary Examiner* — Jermie Cozart
(74) *Attorney, Agent, or Firm* — Shewchuk IP Services, LLC; Jeffrey D. Shewchuk

(57) ABSTRACT

A woven wire braid residing between a polymer inner lumen and a polymer outer lumen transmits control force in a catheter. After braiding the wires, the braid is plated with a metal, such as electroless nickel alloy deposited with a target thickness in a range of 250-1200 micro-inches. The metal plating joins the wires to each other at points of contact which torsionally stiffens the braid. At the same time, the metal plating leaves lengths of the wires unattached between the points of contact, permitting flexibility to the braid due to the unattached lengths between points of contact.

20 Claims, 2 Drawing Sheets

(56) References Cited

U.S. PATENT DOCUMENTS

| | | | |
|---|---|---|---|
| 5,957,910 A * | 9/1999 | Holden, II | A61M 25/005 604/524 |
| 6,143,059 A | 11/2000 | Tangi et al. | |
| 6,213,995 B1 * | 4/2001 | Steen | A61B 18/14 604/527 |
| 6,265,667 B1 * | 7/2001 | Stipes | H01B 7/28 174/102 R |
| 6,281,157 B1 | 8/2001 | Tangi et al. | |
| 6,524,642 B1 | 2/2003 | Leibman et al. | |
| 6,626,889 B1 * | 9/2003 | Simpson | A61L 29/02 604/524 |
| 7,846,503 B2 | 12/2010 | Stark et al. | |
| 8,795,255 B2 | 8/2014 | Jansen et al. | |
| 2009/0126862 A1 * | 5/2009 | Leeflang | A61M 25/0012 156/188 |

* cited by examiner

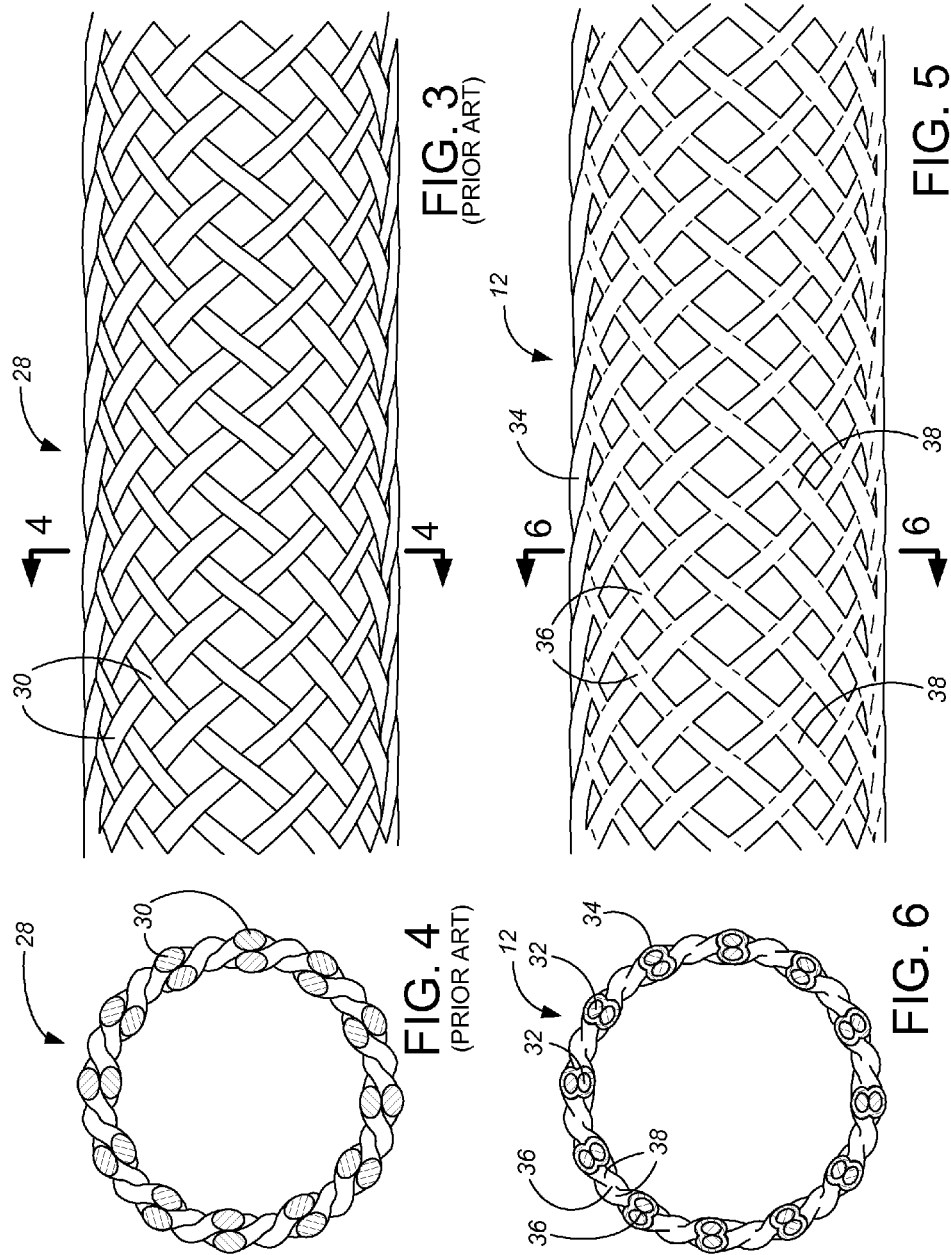

BRAID PLATING METHOD FOR TORSIONAL STIFFNESS

CROSS-REFERENCE TO RELATED APPLICATION(S)

The present application claims the benefit of U.S. provisional patent application Ser. No. 62/072,352 filed Oct. 29, 2014. The contents of U.S. provisional patent application Ser. No. 62/072,352 are hereby incorporated by reference in entirety.

BACKGROUND OF THE INVENTION

The present invention is directed to braided wires having three or more strands, and in particular to braided wires used in catheter construction.

A catheter is a tool used to deliver surgical tools and medical devices to a surgical site via the smallest possible opening into the body. A wire braid is a common structural component of a medical catheter device.

There is advantage in making the wall thickness of the catheter as thin as possible. This permits the largest possible inside catheter diameter while maintaining the smallest possible outside catheter diameter. The catheter must fit within the smallest possible blood vessels in order to access as much of the body as possible, while still having maximal internal capacity to deliver tools and devices to the surgical site.

The catheter must also be able to transmit accurately, the input forces, radial and axial, required to manipulate the catheter and the enclosed surgical tools and supplies. That is the function of the wire braid, which is commonly enclosed between various inner and outer layers of polymeric materials.

U.S. Pat. No. 8,795,255 is directed to a catheter with composite stiffener, and discusses the problems associated with catheter stiffness. For some uses, catheters should be fairly stiff at their proximal end so as to allow the pushing and manipulation of the catheter as it progresses through the body, and yet should be sufficiently flexible at the distal end to allow passage of the catheter tip through the loops and increasingly smaller blood vessels in which the catheter is used. U.S. Pat. No. 5,897,567 also speaks to stiffness, which is a primary attribute desired in the catheter construction. Both of these patents are incorporated by reference for their teachings related to stiffness and flexibility particularly in catheter construction. However, better solutions to obtain the desired balance between stiffness (particularly torsional stiffness) and flexibility are needed, particularly for use in catheter construction.

Separate from the catheter arts, there is archeological evidence that electroplating was conducted as far back as the Bronze Age. In the more recent 20-30 years, an innovation on the theme is the electroless plating chemical reaction. The important distinction is that the electroless nickel chemistries existing today almost always are alloyed with between 3 and 12% phosphorous. This is for increased corrosion resistance on the deposit, such as for use in car bumpers. The phosphorous addition also makes the electroless plated deposit more ductile. As the original chemical reaction was electroplating, the industry may generically use the term "electroplating" as referring to either electroplating or electroless-plating or both.

BRIEF SUMMARY OF THE INVENTION

The present invention is a braid for use in transmitting control force, such as axial and torsional forces in a catheter, typically used between a polymer inner lumen and a polymer outer lumen in the catheter. The braid is woven together from wires, and then plated with a metal. The metal plating joins the wires to each other at points of contact which torsionally stiffens the braid. At the same time, the metal plating leaves lengths of the wires unattached between the points of contact, permitting flexibility to the braid due to the unattached lengths between points of contact.

BRIEF DESCRIPTION OF THE DRAWINGS

FIG. 3 is a side view of a portion of a prior art catheter braid.

FIG. 4 is a cross-sectional view taken along lines 4-4 in FIG. 3.

FIG. 5 is a side view of a portion of a catheter braid in accordance with the present invention.

FIG. 6 is a cross-sectional view taken along lines 6-6 in FIG. 5.

While the above-identified drawing figures set forth a preferred embodiment, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

The present invention is a coating or surface finish applied to a multi-strand braid which acts to lock the strands together at their points of intersection, as well as the braid thereby constructed and its further applicability to catheter construction. While the coating or surface finish could alternatively be provided via other methods (including possibly vapor deposition, plasma spray, etc.), the preferred method of application is via electroless plating, and the remainder of this description will use the term "plating" even if a different application method is used.

Figure 1:
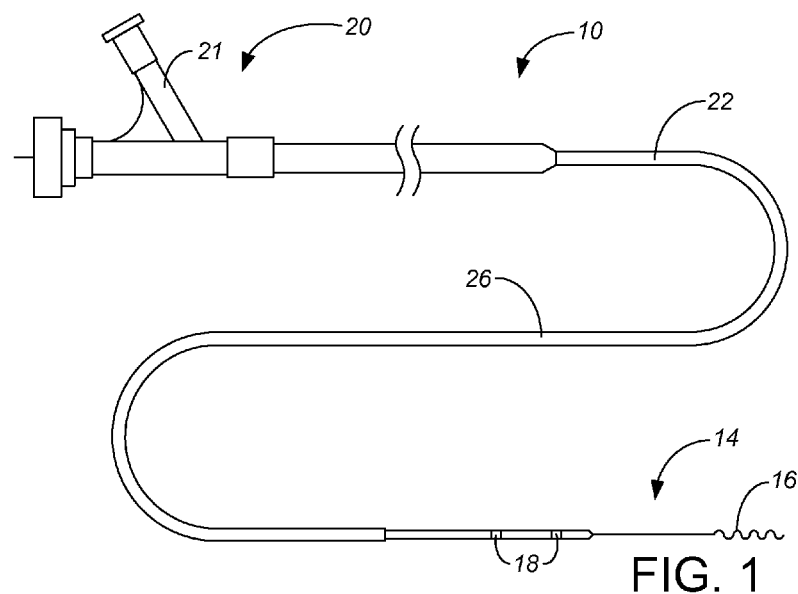
FIG. 1 is a schematic side view of a catheter incorporating the braid of the present invention.

FIG. 1 depicts a catheter 10 utilizing the braid 12 of the present invention, but otherwise including the structure and features commonly associated with modern catheter construction. Such a catheter 10 may be suitable for neurological and peripheral vascular applications, and for other medical applications such as in access and treatment of the heart. The typical configuration shown in FIG. 1 has a distal end or tip 14 which includes the tools or active structures used at the treatment location. A guidewire 16 may extend from the distal end 14 to assist in placement. One or more radiopaque bands 18 may be used to assist in viewing and ascertaining the position of the distal end 14 under fluoroscopy. The proximal end of the catheter 10 includes a luer assembly 20 for guidewire and catheter control and having a fluids access section 21. Between the distal tip 14 and the luer assembly 20 is an intermediate section 22, which may itself have different diameters and differing amounts of flexibility along its length. The catheter 10 must be sufficiently flexible to permit penetration of the extraordinary convolutions of the neurological, vasculature or organ anatomy with minimal trauma. During either positioning or deployment, the intermediate section 22 is used in transmitting control force in the catheter 10 from the control input end 22 to the controlled tip 14. As better depicted in FIG. 2, the intermediate section 22 typically includes an inner polymeric tubing or lumen 24, an outer polymeric tubing or lumen 26, and a braid 12 positioned between the inner lumen 24 and the outer lumen 26. The function of the braid 12 is to assist in transmitting force across the intermediate length 22 of the catheter 10.

FIGS. 3 and 4 depict a catheter braid 28 in accordance with the prior art. The braid 28 generally consists of a number of wire strands 30 which are braided or woven together. In the depicted example, the braid 28 includes twenty-four wire strands 30, twelve wrapped helically in a clockwise direction and twelve wrapped helically in the opposite counter-clockwise direction, but braids of many other numbers of strands, such as sixteen or thirty-two, are also common and equally applicable.

FIGS. 5 and 6 depict a catheter braid 12 in accordance with the present invention. The primary starting material for the braid 12 is metal wire 32, defined by cross sectional shape and dimension(s), and material type. These can be modified across a wide range of values and shapes. The preferred wire material is stainless steel, tungsten, molybdenum, titanium, or nickel-titanium alloys, with the most preferred embodiment being formed of ASTM 304 stainless steel. The wire cross sectional shape may be rectangular or other polygon (having corners), but more preferably is smooth sided (having no corners, round or oval), with the most preferred wire 32 being round. The wire diameter or thickness can be within the range from 0.0001 to 0.01 inches, with a preferred wire 32 being 0.003 inches across. Other common round diameter thicknesses are 0.0005, 0.001 and 0.005 inches. Common rectangular wire thicknesses dimensions are 0.001×0.001, 0.001×0.003 or 0.001×0.005 inches.

At least three strands of wire 32 are woven into the braid 12. The braid assembly is defined by the style of weave, the number of individual elements involved, and the braided density of elements (loosely versus tightly braided), all of which can be varied over a wide range and still be metal coated to result in a decrease in force transmission absorption. Most preferably the braid structure 12 consists of individual wires or wire pairs that are woven into Regular Style which is a one-under-two, over-two pattern. Alternatively the weave can be Diamond Style which is a two-under-two, over two pattern; or a Diamond Half Load which is a one-under-one, over one pattern. The pic count of the braid 12, which is the number of intersections occurring per linear inch of braid, is within the preferred range from 20 to 80. In general, lower pic counts are more flexible and higher pic counts are more torqueable. While FIGS. 3 and 4 depict a prior art braid 28 having the same pic count as the inventive braid 12 shown in FIGS. 5 and 6, the present invention permits lower pic count braids to increase torqueability, and that increase in torqueability is preferably achieved without a corresponding decrease in flexibility. In the preferred method of making the invention, braid elements 32 are dispensed from spools of material (not shown) and assembled into a braid assembly by means of a braiding machine (not shown).

The braid 12 is preferably cut prior to plating to a desired force transmission length, such as at least 12 inches, and more preferably within a range of 36 to 72 inches, generally matching the length needed in the resulting catheter 10. Alternatively, the braid 12 can be continuously plated and cut after plating and possibly further manufacturing steps to result in the desired braid length.

After weaving the braid, the braid is coated with a metal coating 34, forming a mechanical bond between adjacent braid elements 32 at their points of intersection 36. The coating or plating 34 is defined by composition and amount applied. The composition can be varied over a wide range and the thickness can be varied over a range to attenuate the amount of force absorption. The coating 34 is preferably a nickel based material, and more preferably is a nickel/phosphorous alloy with a phosphorous content within the range of 3 to 12% by weight, more preferably within the range of 5 to 12%, with a most preferred phosphorous content being about 10.3%. Alloying the nickel plate with phosphorous increases the flexibility of the resulting coated braid assembly 12. If desired, inert particles such as teflon, silicon carbide or boron nitride could be added and co-deposited with the metal coating 34.

The thickness of the nickel coating 34 is within the range from as low as 10 micro inches (0.000010") to as high as 5000 micro inches (0.005000"), and more preferably within the range from 250 micro inches to 1200 micro inches. This range permits flexibility in deciding the optimal combination of cost of production and degree of torqueability specific to each user's needs and demands. Preferred thickness targets are 250, 500 and 1000 microinches of thickness, with the most preferred coating thickness target being 750-1000 microinches.

As an alternative to using nickel as the primary metal in the coating 34, other metals in the coating 34 could also provide enhancements to torqueability. Silver and copper are coating metals that are particularly considered as low cost hypo-allergenic options, and gold is a coating metal that is particularly considered for its corrosion resistance and biocompatibility.

Once assembled or woven, the braid is cleaned and immersed in a solution of dissolved metal, attaching to and covering the entire exposed surface of the braid assembly 12 and braid elements 32. The nickel coating 34 is applied from a solution of dissolved metal. The attachment mechanism can occur either using an electrical current to drive the attachment reaction, or more preferably by utilizing an autocatalytic chemical reaction requiring no electrical motive force, i.e, an electroless nickel plating reaction. A significant advantage of the electroless nickel plating process is the ability to produce deposits with uniform thickness on parts with complex geometries and shapes such as the braid surface. As examples of electroless plating processes and compositions, see U.S. Pat. Nos. 3,123,484; 3,148,072, 3,338,726, 3,719,508, 3,745,039, 3,754,939, 3,915,717, 4,152,164, 6,143,059, 6,281,157, 6,524,642 and 7,846,503, all incorporated herein by reference.

The function of the braid 12 is to assist in transmitting the motion input from one end (proximal) of the braid 12 to the opposite end (distal). Without the plating in the prior art configuration shown in FIGS. 3 and 4, the braid elements or wires 30 can slide past each other when an axial or radial force is applied to one end of the braid 28. The force is less than fully transmitted along the length of the braid 28 due to the pliant nature caused by the relative motion of one braid element 30 sliding along another braid element 30. Input losses occur as a result of the relative sliding motion of braid elements 30 past each other.

The present invention increases the ability of the braid 12 to transfer input forces (proximal) to "other end" output forces (distal), in torque, axial and radial vectors, while simultaneously decreasing the amount of input force which is absorbed in unintended deformation of the braid assembly 12. The plating 34 applied to the braid 12 causes the points of contact 36 of the braid wires 32 to become solidly connected, while leaving lengths 38 of the braid wires 32 between points of contact 36 unattached to retain flexibility. The coated braid wires 32, though still able to freely bend between points of contact 36, can no longer slide past each other. The increased force transmission by metal plate fusing of points of contact 36 of the braid wire permits a small diameter wire to be used for the braid 12. This results in a large inner diameter to the entire catheter assembly without a corresponding increase in outer diameter of the entire assembly. More functional equipment can be used in the catheter 10 and still fit the smaller anatomical vessels.

The present invention improves the ability of the catheter 10 to transmit axial and radial forces, while maintaining minimally thin catheter wall thickness. The preferred embodiment relates to a range of overall catheter thickness from 1 French (0.013 inches) to 20 French (0.262 inches), and particularly to overall catheter thicknesses from 1 French (0.013 inches) to 8 French (0.105 inches). In the prior state of the art, smaller French dimension catheters sacrifice some degree of torqueability as the diameter of the braid wire decreases. The improvement in torqueability with the metal plating is particularly beneficial for small diameter braids 12.

The plating 34 applied to the braid elements 32, once assembled into a braid assembly 12, reduces the pliancy of the braid assembly 12 which results in a more complete and accurate axial and radial force transmission from proximal to distal ends. The invention reduces the parasitic absorption of forces by the braid structure. Particularly when smaller diameter wires 32 are used in the braid structure 12 (i.e, when the plated diameter of the wires 32+34 corresponds with prior art unplated wire diameter 30, as shown in the comparison between FIGS. 4 and 6), the invention does not reduce the flexibility of the braid structure 12.

The plating 34 attaches strongly to all exposed surfaces of the braid wires 32 and also forms a mechanical bond between adjacent braid wires 32 at, and adjacent to, the points of element intersection 36. Once bonded together, adjacent elements 32 can no longer slide past one another as a response to a force input at one end of the assembly. The result is a force transmitting braid assembly 12 which more completely and accurately transmits the input forces (particularly torsional and axial forces) to the distal end of the assembly.

Figure 2:
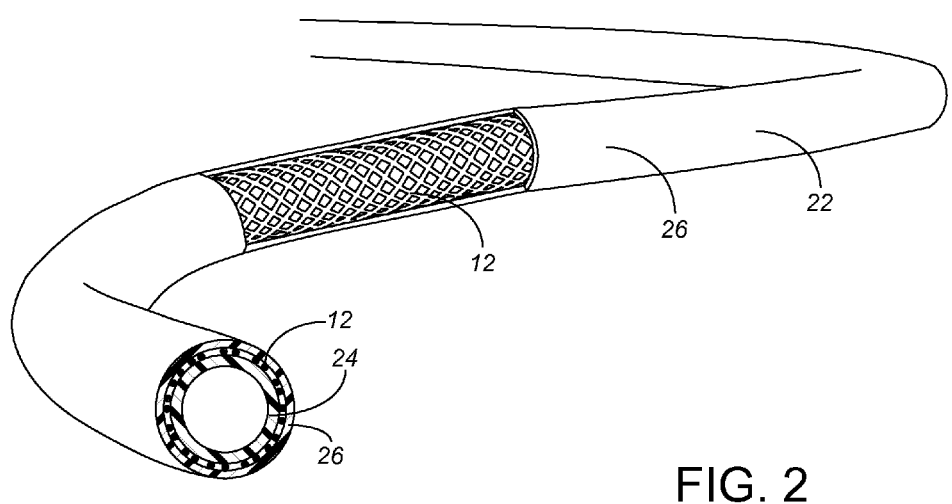
FIG. 2 is a view depicting the force transmission section of the catheter of FIG. 1, with a portion of the outer polymer lumen broken away to show the braid of the present invention.

As best depicted in FIG. 2, the coated braid assembly 12 is installed into a catheter assembly, sandwiching the braid 12 between the inner lumen 24 and the outer lumen 26 to form a structural, intermediate component 22. The structural component 22 provides increased accuracy in guiding the catheter 10 to its destination. Further, once at the intended destination, the increased torque transmitting ability of the braid assembly 12 permits a more accurate manipulation of the catheter 10 during the activity for which the catheter 10 is intended.

Although the present invention has been described with reference to preferred embodiments, workers skilled in the art will recognize that changes may be made in form and detail without departing from the spirit and scope of the invention. For instance, while the invention is particularly described with reference to a catheter braid 12, the invention can be used for the same force transmission improvement for any device which benefits from increased force transmission effectiveness of a braided assembly, i.e. for and flexible shaft torque transmission device or flexible drive shaft.

What is claimed is:

1. A method of forming a braid for use in transmitting control force in a catheter from a proximal control input end of the catheter to a distal controlled tip of the catheter, the method comprising:
   braiding at least three wires together, each wire having a wire thickness and the at least three wires braided together extending across a force transmission length; and
   plating the at least three wires braided together with metal plating throughout the force transmission length, with the metal plating joining the wires to each other at points of contact, the metal plating being deposited with a plating thickness which is at least 10 micro-inches and no greater than 5000 micro-inches, such that the metal plating leaves lengths of the at least three braided wires unattached between the points of contact;
   wherein the metal plating torsionally stiffens the braid by transmitting torque across the joined points of contact throughout the force transmission length, with the metal plating permitting flexibility to the braid due to the unattached lengths between points of contact.

2. The method of claim 1, wherein the metal plating extends across at least 12 inches of force transmission length of the braid.

3. The method of claim 1, wherein the wires are woven in a weave selected from Regular Style, Diamond Style and Diamond Half Load, and in which the pic count of the braid is within the range from 20 to 80.

4. The method of claim 1, wherein the plating act is achieved by immersing the wires braided together in a solution of dissolved metal.

5. The method of claim 4, wherein the plating act uses an electrical current to drive the attachment reaction.

6. The method of claim 4, wherein the plating act uses an electroless plating reaction.

7. The method of claim 1, further comprising cutting the wires braided together to length prior to the plating act.

8. The method of claim 7, wherein the wires braided together are cut to a length within the range of 36 to 72 inches prior to the plating act.

9. The method of claim 1, wherein the metal plating is a nickel based material.

10. The method of claim 9, wherein the nickel based material is a nickel/phosphorous alloy with a phosphorous content within the range of 3 to 12% by weight.

11. The method of claim 1, wherein the wire is formed from a material selected from stainless steel, tungsten, molybdenum, titanium and nickel-titanium alloy, wherein each wire in the braid has a wire thickness in the range of 0.01 to 0.0001 inches, and wherein the plating thickness is in the range of 250-1200 micro-inches.

12. The method of claim 1, further comprising sandwiching the braid between an inner lumen and an outer lumen in the catheter, wherein the outer lumen has an outer thickness from 1 French (0.013 inches) to 20 French (0.262 inches).

13. A method of torsionally stiffening a control force transmission unit, the method comprising:
   providing a plurality of wires assembled together, each wire having a wire thickness and the wires assembled together extending across a force transmission length; and
   plating the wires assembled together with metal plating throughout the force transmission length, with the metal plating joining the assembled wires to each other at points of contact, with the metal plating leaving lengths of the assembled wires unattached between the points of contact;

wherein the metal plating torsionally stiffens the plated assembly by transmitting torque across the joined points of contact throughout the force transmission length, with the metal plating permitting flexibility to the plated assembly due to the unattached lengths between points of contact.

14. The method of claim 13, wherein the wire thickness of each wire is in the range of 0.01 to 0.0001 inches.

15. The method of claim 13, further comprising sandwiching the plated assembly between an inner lumen and an outer lumen in a catheter, and wherein the outer lumen has an outer thickness from 1 French (0.013 inches) to 20 French (0.262 inches).

16. The method of claim 13, wherein the metal plating is a nickel based material.

17. The method of claim 16, wherein the nickel based material is a nickel/phosphorous alloy with a phosphorous content within the range of 3 to 12% by weight.

18. The method of claim 13, wherein the plating thickness is in the range of 250 to 1200 micro-inches.

19. The method of claim 18, wherein the wire thickness is 0.003 inches, and wherein the plating thickness has a target in the range of 750-1000 micro-inches.

20. The method of claim 13, wherein the wires are formed from a material selected from stainless steel, tungsten, molybdenum, titanium and nickel-titanium alloy.

* * * * *